United States Patent [19]

Way

[11] 4,252,772
[45] Feb. 24, 1981

[54] APPARATUS FOR THE RECOVERY OF VAPORIZED PHTHALIC ANHYDRIDE FROM GAS STREAMS

[76] Inventor: Peter F. Way, P.O. Box 276, Boxford, Mass. 01921

[21] Appl. No.: 942,616

[22] Filed: Sep. 15, 1978

[51] Int. Cl.³ .................... B01D 7/00; B01D 59/02; C07D 307/89
[52] U.S. Cl. .................. 422/244; 55/82; 55/269; 55/344; 260/346.7; 62/12
[58] Field of Search ............. 55/27, 80, 81, 82, 209, 55/269, 344; 422/244; 62/12; 165/2, 61, 108, DIG. 16, 105, DIG. 12; 260/346.7, 706

[56] References Cited

U.S. PATENT DOCUMENTS

| | | | |
|---|---|---|---|
| 1,725,906 | 8/1929 | Gay ........................... | 165/DIG. 12 |
| 1,842,263 | 1/1932 | Gobert ....................... | 55/82 |
| 2,076,003 | 4/1937 | Kniskern ................... | 422/244 |
| 2,455,314 | 11/1948 | Pietzsch ..................... | 55/82 |
| 2,590,145 | 3/1952 | Aronson ..................... | 62/12 |
| 2,665,840 | 1/1954 | Powell ........................ | 165/108 |
| 3,602,429 | 8/1971 | Levedahl et al. ........... | 165/105 |
| 3,766,971 | 10/1973 | Baum ......................... | 55/82 |
| 4,033,406 | 7/1977 | Basiulis ...................... | 165/105 |
| 4,062,871 | 12/1977 | Gehrken et al. ............ | 260/346.7 |
| 4,127,163 | 11/1978 | Reti ............................ | 165/105 |

FOREIGN PATENT DOCUMENTS 2656030  6/1978  Fed. Rep. of Germany .......... 165/105

Primary Examiner—David L. Lacey

[57] ABSTRACT

Phthalic anhydride is recovered from gases in a multiple heat-pipe exchanger system, one or more for condensing phthalic anhydride from gases containing vapors thereof and one or more simultaneously melting out the condensed phthalic anhydride solids, the exchangers being switched in alternate cycles to melt out from the surfaces of the exchanger tube ends on which the phthalic anhydride solids were first accumulated, and to condense phthalic anhydride solids in the exchanger or exchangers from which the phthalic anhydride was cleared by melting out. The cooling of opposite heat-pipe exchanger ends to recover phthalic anhydride is economical and efficient with ambient air, either alone or with some warm recycle exchanger air to adjust the cooling temperature; and the heating to melt out accumulated phthalic anhydride is effected with hot gases, such as combustion gases, preferably by incineration of residual phthalic anhydride tail gas from which the phthalic anhydride was condensed, or other hot combustion gases, but other sources of heating the air or gases may be optionally substituted. Important advantage is present in superior heat exchange efficiency using the heat-pipe exchanger for this service, in the ready switching from heating to cooling of such exchangers for alternate operation in both condensing and melting out modes, in the elimination of intermediary heat transfer media and the separate auxiliary equipment required for the heating and cooling cycles, in the utilization of waste heat from combustion gases, and in the great economy for phthalic anhydride storage tank vent condensers through elimination of both cooling water and steam requirements.

5 Claims, 1 Drawing Figure

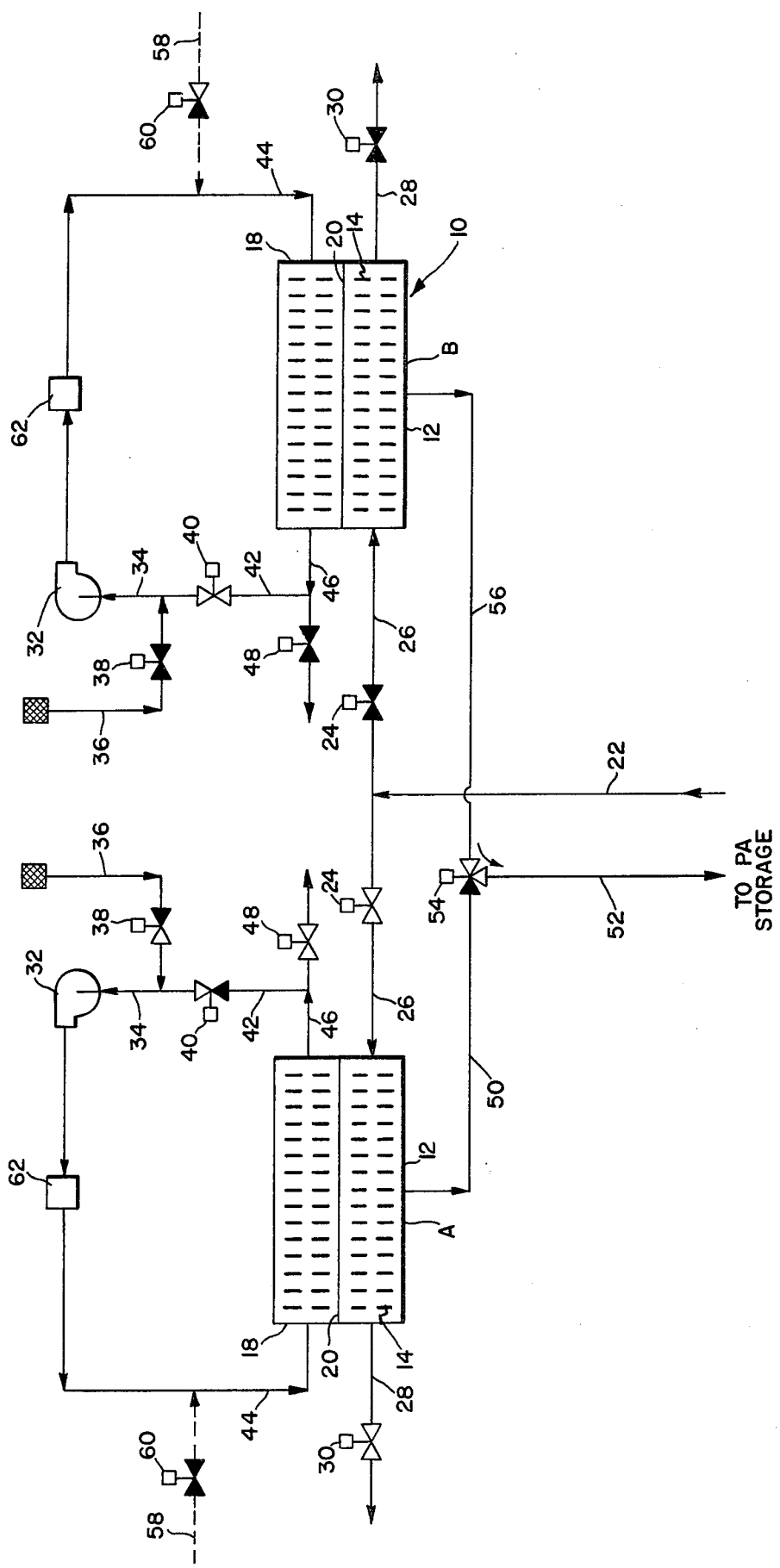

APPARATUS FOR THE RECOVERY OF VAPORIZED PHTHALIC ANHYDRIDE FROM GAS STREAMS

This invention relates to purification by condensation and recovery of phthalic anhydride (PA) from gas streams, in which it exists as a condensable vapor, either as formed by oxidation of naphthalene or o-xylene admixed with other oxidation products or as released by PA storage tanks in the breather vent gas, or as generated by any manufacturing process, in a heat transfer system of improved efficiency; and more particularly, recovery of the phthalic anhydride in a heat-pipe switch condenser system, comprising a group of heat pipes which in alternate operation the phthalic anhydride is condensed to solids in one mode, while the condensed solid phthalic anhydride is melted out in a simultaneously operated companion unit, the units being cyclically alternated, with great heat economy both with this more efficient exchanger system and by using air as the cooling phase for the condensation of PA solids and by using hot combustion gas or heated air for melting the condensed PA solids, especially using waste heat such as incinerator exhaust gas for supplying the heat needed for melting out to recover the condensed PA solids in the companion mode, both process and apparatus.

The process and apparatus hereof becomes more efficient for the production and recovery of phthalic anhydride and is greatly improved in economy over the prior art practices. The heat-pipe exchanger, although known per se as a type of exchanger, has not been used either for PA recovery or comparable systems. Moreover, the heating and cooling systems used in the present PA recovery and alternately ambient air for condensing the PA vapor, and hot gases, usually from combustion of waste gases, particularly even exhaust gases available from incineration of PA reactor tail gas, for supplying heat needed to melt the condensed PA solids. Particularly, the improved economy in the construction and operation of the system is available from the fact that no circulating water or other low temperature heat transfer medium is needed to cool the gas and condense the PA to the solid state, nor is steam or other high temperature heat transfer medium needed to melt out the recovered solid, so the heat exchanger system can be located and operated, not only without these auxiliary heat transfer media systems, an important economy in itself, but also it can be located in places where cooling water is unavailable or costly.

PRIOR ART

In prior art practices the condensation of PA to a solid state is typically performed in shell and tube heat exchangers, or in arrangements of tube bundles in large enclosures with alternate cooling and heating of the tube surfaces by passage of a heat transfer medium through the tubes, one unit of which cools the gas stream to condense the PA vapor on the tube surfaces, and after selected periods the unit is alternated to the other mode of passing a second heat transfer fluid through the tubes at a temperature high enough to melt the PA.

There are three types of phthalic anhydride gas streams conventionally to be treated, the so-called (a) reaction gas stream formed in catalytic oxidation of naphthalene of o-xylene; (b) vent gas stream which emanates from PA storage tank breather vents; and (c) any manufacturing process gas stream that generates PA-laden vapors, each posing the problem of condensing the gaseous phthalic anhydride to solid form, and the subsequent warming of that solid condensate to recover the solid phthalic anhydride in molten form.

TEMPERATURES

In the case of reaction gas, the initial temperature of the gas PA stream is in the approximate range of 135°–250° C. and the exit gas temperature to which the gas stream is cooled is usually in the range of 45°–75° C., preferably to about 55°–65° C. Vent gases reach a lower entering temperature, such as 135°–160° C. with the desired exit gas temperature in the range of 40°–60° C. The process gas streams typically have an entering temperature in the range of 135°–200° C., depending upon the source of the process gas. Consequently, for the stated low exit temperature the exchanger surfaces at the outlet end should be maintained in the range of about 35°–60° C. with higher values applicable to reaction gas and lower values to vent and process gas streams.

The surface temperature of the exchanger required for melting the deposited PA solids is in the range of 135°–190° C. from any of these sources. Merely by considering the extreme temperatures to be needed in each exchanger operation from low to high as stated, separate systems are required for the two levels of heat transfer medium to meet these two ranges, i.e. as low as 35°–60° C. and as high as 135°–190° C. These separate low temperature and high temperature fluid circulating systems that are needed for conventional exchanger practice typically depend on cooled water and high pressure steam, or a cold and a hot circulating fluid, and that was the practice of the prior art in making such temperatures practically available for handling these PA recovery streams.

AUXILIARY UNITS

Moreover, the low temperature circulating system must further be provided with means for dissipating the heat removed from the hot PA gas stream, and conventionally heat exchange with cooling water was employed for this, but the cooling water also required a cooling tower for dissipating the heat. The high temperature heat transfer system, in contrast, required supply of high level heat to the circulating fluid, and this could be accomplished only by an indirect gas fired or oil heater, or by use of a boiler in the case of heating with steam.

It is clear that the facilities required in the prior art to alternately cool and heat the heat exchangers involved great initial investment, as well as high operating and maintenance costs. Moreover, conventional indirect exchangers of that type have low thermal efficiencies with accompaning low economy. In the case of reaction gas it is most uneconomical to utilize available waste heat in the tail gas incinerator exhaust usually associated with such systems. Vent gas streams in most instances require processing at remote tankage areas where cooling water is not available and a cooling tower for this purpose is needed. The isolated locations of such equipment items further present maintenance problems complicated by the isolation.

Heat-pipe exchangers for PA recovery, according to the present invention, simplify the heat exchanger system by eliminatng the need for an intermediary low temperature heat transfer system, such as cooling water or other medium, and impart greater thermal efficiency to the system, so that particularly in the case of reaction gas, the available waste heat from the reaction process is useful in the melting step to virtually eliminate the need for other fuel. In consequence, the present invention provides lower initial investment, lower operating costs and substantial fuel savings. Each of these objects are achieved in the novel heat exchanger system using the heat-pipe exchanger both in recovery and melting of PA applied in alternate operating modes. It uses air directly as the cooling medium and either heated air or hot exhaust gas for the heating medium in contrasting great efficiency and economy for this purpose.

The heat-pipe exchanger hereof seems uniquely adapted for recovery of PA from the several gas streams listed to achieve these benefits. The term "heat pipe" as commonly understood, refers to a conduit, pipe, duct or tube, usually but not necessarily circular in cross-section, and sealed at both ends to provide a closed circuit. It includes a wick structure within the duct or tube and usually upon the inside surface, and the tube is evacuated and charged with a small quantity of a working fluid. Typical working fluids are the common fluorocarbon refrigerants known as the R-series such as R-11 and R-113, and hydrocarbons such as toluene. Heat absorbed at one end of the heat pipe causes the working fluid to vaporize, and the vapor flows under the driving force of the slightly increased pressure to the cold end of the tube where it condenses and thereby releases its heat to the pipe wall. The circuit is completed by the condensed working fluid returning to the hot end of the heat pipe by capillary movement through the internal wick structure. A heat-pipe exchanger includes a substantial multiplicity of such heat pipes, arranged so that all of the cold ends are exposed externally to the gas stream being heated, and the opposite hot ends are exposed to the gas stream from which heat is being extracted, in gas-to-gas heat exchange of the two streams, each conducted simultaneously through adjacent enclosures about opposite tube ends in countercurrent flow with the heat pipes in a bundle extending into separate enclosure ducts, one for each stream, and having a common dividing wall. The total heat-pipe exchanger consists of such tubes sized to accommodate the exchanger needs of the streams to be treated. The advantages of the heat-pipe exchangers applicable to PA recovery are:

1. They operated with small temperature difference between cold and hot ends of the heat pipes under conditions of high heat transfer rates;
2. They have high thermal efficiency in gas-to-gas exchange at low pressure drops;
3. They have large surface areas that are available in heat-pipe bundles of reasonable dimensions through the use of extended surface or finned tubes for the accumulation of the condensed PA solids;
4. Bidirectional control of the aspect of heat pipe operation is an inherent feature such that the heat transfer can be reversed by reversing the hot and cold ends, in this case by switching the hot and cold gas or air streams. 5. The working fluid contained in the sealed pipes can be readily selected as to be operable over the full temperature range of both PA condensing and melting steps from about 35°–225° C.

Because of these characteristics, ambient air is useful directly as a cooling gas stream for the PA condensing step. To avoid cooling reaction gas below a temperature approaching the water dew point of about 35°–40° C., a portion of heated exit air is recycled to the blower and mixed with incoming ambient air to maintain a combined inlet temperature in the range of 30°–55° C., preferably 35°–40° C.

Again, heated air or gas is useful as the high temperature heating medium applied during the melting step of the PA. For this several options are available. One such is to recirculate through the air side of the heat-pipe exchanger heated air at a temperature in the range of about 150°–300° C., preferably 175°–225° C. The air is heated by several alternate means, using a gas or oil fired in-line burner, or electrically using an electric resistance heater, or using a steam coil. A further option is available with reaction gas systems that employ a tail gas incinerator by using the incinerator exhaust gases adjusted to a temperature range of 200°–300° C. as the heating medium for melting the PA. Typically, the incinerator exhaust gases will have a heat content sufficient to supply all of the necessary melt-step heat in a reasonable adjusted cycle time. Moreover, an auxiliary burner may be provided to pass combustion gases into the hot gas duct to supplement the heat as needed for the usual cycle time, or even to accelerate to shorter periods the melting time required to melt the PA using a higher temperature as provided by the extra heat, and periodically to remove other high melting impurities that may accumulate on the heat transfer surfaces for short excess-temperature heating periods. Still another option available for treatment of reactor gases, useful in the absence of a tail gas incinerator, is to use any available hot flue gas stream from an oil, gas, or coal fired heater or steam boiler.

In vent gas applications, heating of the air for the melting step is most readily provided by use of an electric resistance heater, although a steam heater can also be used, with total air recirculation to minimize the energy requirement. In these several alternatives, the present method allows complete elimination of the need for separate cooling water systems, usefully serving remote tankage area locations, and it also makes possible elimination of steam supply and steam condensate systems.

Wide variations in methods for designing gas-to-gas heat-pipe exchangers for other services are known. In designing for condensation of the accumulated solid PA while maintaining the desired thermal efficiency and acceptable pressure drop, it is found that the number of tube rows may be increased in depth by a factor of 1.5 to 5, preferably 2 to 3 with respect to the usual gas-to-gas exchanger requirements. Alternatively, it is preferred to increase the face area of the PA condensing side of the exchanger by a similar factor, or to increase the face area in combination with an increase in the number of tube rows, to minimize pressure buildup on the condensing side. In this manner vent gas, process gas or reaction gas streams containing vaporized PA in the typical concentrations, ranging from 30–75 g/Nm$^3$ at a temperature in the range of 135°–250° C., can be cooled with ambient air in a heat-pipe exchanger to an exit temperature of 45°–75° C., preferably 55°–65° C. with a PA recovery efficiency of greater than 99% and the condensed solid is easily and efficiently melted off of the exchanger surfaces either by heated air or an exhaust gas stream or other heat alternatives listed above.

The invention is further described in relation to the drawings wherein:

The figure schematically shows, in plan view, an arrangement of a heat-pipe switch condenser system with one exchanger A in the condensing mode and the second heat-pipe exchanger B of the same system in the melting mode. Both heat-pipe exchangers 10 are each disposed in a divided housing 12 and 18. A number of heat-pipes are disposed in a bundle 14, extending horizontally, or at a slight angle, from one housing 12 to the other housing 18, separated by a partioning wall 20 which prevents any interchange of exchanger gases from the housing 12 to the housing 18. The incoming hot gas steam, either reaction gas, vent gas or process gas carrying recoverable PA enters through duct 22, the left valve 24 being opened and the right closed. The PA-laden stream passes into the housing 12 through the portion of exchanger bundle 14 contained therein, referred to as the "condensing side." at a temperature in the ranges stated above, leaving through duct 28, the valve 30 being open.

The left blower 32 draws ambient air through ducts 34 and 36 as well as recycle flow in line 42, the valves 38 and 40 being adjustably opened. The proportioned flows are adjusted by the settings of valves 38 and 40 to provide that inlet air at a temperature adjusted by recycle to housing 18 as cooling air to pass through the opposite portion of bundle 14, referred to as the "air side." The entering cooling air from line 44 at the left side of the exchanger thus passes in countercurrent flow to the PA-laden gas, and by the mechanism of heat transfer characteristic of heat pipes described above, cools the gas for condensing PA, the residual gas leaving at 28. The heated air from the air side 18 leaves by way of line 46, the valve 48 being opened. In an alternate melting stage a duct 50 for removal of melted PA after first depositing in mode A operation is connected to a duct 52 through a valve 54 for disposal of the molten PA withdrawn to storage. The duct valve 54 is closed to exchanger A during the condensing cycle, while the PA is accumulated as solid sublimate therein.

As the hot entering PA-laden gas passes through the condensing side of the heat-pipe bundle 14, it transfers its heat to the heat pipes and condenses the PA vapor to the solid state. The heat extracted in gas cooling and in the condensation of the PA is conducted by vaporization of the heat pipe internal working fluid to the opposite end of the tube bundle 14 where it is cooled and condensed by ambient air passing through housing 18. The lower temperature cooling air stream passing through the air side from line 44 cools and condenses the internal working fluid which then flows by capillary action through the wick structure therein, returning as liquid working fluid to the PA condensing side of heat-pipe bundle 14 contained in housing 12. A portion of the air heated in passage through the air side leaves by way of duct 46 and another portion controlled by valve 40 is recycled through line 34 for admixture with fresh ambient air to provide a temperature control for the entering ambient cooling air in line 44. During the cooling of the PA-laden reaction gas, the PA is condensed as a solid on the heat-pipe tube surfaces in the condensing side. Somewhat prior to the point at which the accumulated solids adversely affect the heat transfer or the pressure drop, the exchangers are each switched to the alternate mode, that is, mode A formerly condensing PA is switched to melting mode B and mode B formerly melting is switched to condensing PA. In this illustrative drawing, both left and right hand sides of FIG. 1 have similar simultaneously operating, one to condense PA and the other to melt and remove the condensed PA solids, shown in the figure as mode A on the condensing cycle and B on the melting cycle, which are alternately switched to the opposite cycle periodically.

During the melting cycle exchanger B is isolated by valve 24 and the 3-way valve 54 is positioned to allow flow between ducts 56 and 52 for discharge of the melted PA. In the case of heat being provided by hot combustion gas or incinerator exhaust gas (combustion equipment and incinerator not shown), this hot gas stream flows through duct 58, valve 60 being open, enters the air side housing 18 of exchanger B through line 44, and exits through valve 48, the recycle valve 40 being closed. The direction of heat transfer in the heat pipes is now reversed from that of the condensing mode. Heat is extracted from the hot gas stream passing through the air side in housing 18, causing the internal working fluid in the heat pipes to vaporize and to flow to the other side of the tube bundle contained in housing 12, on the external surfaces of which is deposited the solid PA condensed during the previous cycle. The condensing working fluid raises the temperature of the tube surfaces sufficiently to melt the accumulated PA as defined above. The condensed working fluid in the heat pipes then returns to the hot ends of the tube bundle in the air side to complete the internal flow cycle as described above.

In the alternate case of heat being provided by heater 62 (right side), which can be a gas or oil fired inline burner, a steam coil, or an electric resistance heater, blower 32 is used to recycle the heated air stream through duct 44, exchanger housing 18, returning to the blower through ducts 42 and 34, and valve 40, valve 38 being closed.

It will thus be observed that the system illustrated comprises equivalent exchangers, one of which is operating in condensing mode A simultaneously with the other exchanger operating in melting mode B. The system described herein, however, is not limited to using heat-pipe exchangers in pairs. In special cases of intermittent opertion, a single exchanger may be employed. On the other hand, for large reaction gas installations, the system may comprise three or more exchangers, either in a balanced configuration with an equal number of exchangers alternately in mode A and mode B, or an unbalanced configuration with several exchangers in mode A and with a smaller number operating alternately in mode B on a shorter cycle time.

EXAMPLES

EXAMPLE 1

Reaction gas formed by catalytic oxidation of naphthalene flowing at a rate in the range of 10,000–20,000 Nm$^3$/hr., typically 17,500 Nm$^3$/hr., at a temperature of 145° C. and containing 48.4 g/Nm$^3$ of phthalic anhydride (PA) vapor is passed into a mode A operating heat-pipe exchanger as shown in the figure. It is cooled in the exchanger to an outlet temperature of 60° C. to condense 99+% of the PA, depositing PA solids upon the tube surfaces of the condensing side of the heat-pipe exchanger. The ambient air circulated through the air side of the exchanger is flowing at a rate of 20,000–40,000 Nm$^3$/hr., typically 36,000 Nm$^3$/hr., adjusted to an exchanger inlet temperature of 38° C. by partial recycle of outlet air. The exchanger face dimensions on the condensing side of the exchanger are 3.66 m by 3.05 m and on the air side, 2.44 m by 3.05 m. The tubes with an extended surface area of 0.59 m$^2$/m are arranged in two banks of eight rows deep, each containing 208 tubes. The air blower has a power requirement of 10–20 KW. In mode B the exchanger for the melting step passes tail gas incinerator exhaust with a temperature of 204° C. at a rate of 10,000–20,000 Nm$^3$/hr, typically 18,000 Nm$^3$/hr, and which is circulated through the air side of the heat-pipe exchanger to warm the tube surfaces to a temperature of 166° C. in about twenty minutes, at which temperature the deposited PA solids of mode A are melted and discharged from the exchanger. The total cycle time is about ninety minutes for deposition and melting out at these rates, forty-five minutes for each mode.

EXAMPLE 2

Vent gas from PA storage tanks containing 41 g/Nm$^3$ of vaporized PA, at a rate of 20–50 Nm$^3$/hr, typically 34 Nm$^3$/hr, and a temperature of 150° C., is cooled in mode A operation to 49° C. condensing 99+% of the contained PA on the dual heat-pipe exchanger system as shown in FIG. 1. It is operated with the following characteristics: Ambient air is circulated through the air side of the heat-pipe exchanger at a flow rate of 200–500 $Nm^3$/hr, typically 345 $Nm^3$/hr, adjusted to an inlet temperature of 38° C. by partial air recycle. The face dimension of the condensing side and the air side of the exchanger are 0.30 m by 0.24 m each. The heat pipes with an extended surface area of 0.59 $m^2$/m are arranged in a single bank with a depth of fourteen rows for a total of fifty-six tubes. The maximum air power requirement is 0.3 KW. For the melting step mode B, the air is passed at 200–500 $Nm^3$/hr, typically 345 $Nm^3$/hr, at a temperature of 177° C. and circulated through the air side using an electric resistance heater as the source of energy for heating the air. The tube surfaces reach a temperature of 166° C. in about fifteen minutes. The PA condensing step of mode A is applied over a period of 4 to 8 hours, typically six hours, and the melting step is completed in forty-five minutes.

As thus described, phthalic anhydride is recovered in a two mode system, condensing the PA from commercially available streams, such as reaction, vent or process gases, by cooling in a heat-pipe exchanger or exchangers for deposition of the PA in yields of better than 99%, using ambient air or ambient air mixed for temperature adjustment with recycle air, and preferably simultaneously the deposited PA sublimate is separately melted in the same type of exchanger or exchangers, preferably in alternate cycles using ambient air for cooling and heated ambient air or combustion gases to melt the PA for recovery in a heat-pipe exchanger system with high operating efficiency.

The system may be modified, as will occur to one skilled in the art, for application of known variations of heat pipe structures and operations in the general exchanger art in the recovery of phthalic anhydride, and it is intended that the description and examples be regarded as illustrative and not limiting, except as defined in the claims:

I claim:

1. A heat-pipe exchanger system for condensing sublimable solids such as phthalic anhydride or the like from vapor streams and then remelting the condensed sublimate solids for recovery thereof comprising a pair of housings disposed adjacent to each other and separated by gas tight partition into an air-side housing through which cooling or heating fluid such as air or gas may be passed and a condensing-side housing through which sublimate-laden vapors may be passed, condensed to a solid and then remelted in alternate cycles and means for withdrawing molten sublimate therefrom, each housing side having an inlet and outlet duct, blower means connected to the inlet duct of said air-side housing, and valve means in said inlet and outlet duct controlling the fluid flow through each housing, for independent flow control of hot and cold exchange fluid flow through each housing, heat-pipe exchanger tubes comprising evacuated tubes having a heat-pipe working fluid therein mounted horizontally with their opposite exchanger tube ends extending through said partition into one of said housings for heat exchange contact with the cooling or heating gases, vapors, or condensed solids therein, said valves, ducts and blower means comprising a means for independently flowing said sublimate-laden vapors through said condensing-side for sublimate condensation and for flowing air or gas cooling or heating fluids through the air-side housing with controlled air or gas recirculation to provide selected temperature adjustment, with operation in either a cooling-condensing cycle or a heating-melting cycle and means for heating the air or gas flowing through said air-side housing when the exchanger is on the melting cycle.

2. The apparatus as defined in claim 1, wherein the said heating means for heating air or gas to supply controlled heat to the air-side exchanger tube ends during the melting cycle comprises a burner or an electric heater, or a steam heating coil.

3. The apparatus as defined in Claim 1, wherein the heat-pipe tubes contain a wick structure to aid in the transport and distribution of the condensed working fluid within the tubes.

4. A heat-pipe exchanger system comprising a duplex assembly of paired exchanger housings, each housing pair operative for condensing sublimable solids such as phthalic anhydride or the like from vapor streams and then remelting the condensed sublimate solids for recovery thereof, said paired exchanger housings disposed adjacent to each other and separated by gas tight partition or into an air-side housing through which cooling or heating fluid such as air or gas may be passed and a condensing-side housing through which sublimate-laden vapors may be passed, condensed to a solid and then remelted in alternate cycles and means for withdrawing molten sublimate therefrom, each housing side having an inlet and outlet duct, blower means connected to the inlet duct of said air-side housing and valve means in said inlet and outlet duct controlling the fluid flow through each housing, for independent flow control of hot and cold exchange fluid flow through each housing, heat-pipe exchanger tubes comprising evacuated tubes having a heat-pipe working fluid therein mounted horizontally with their opposite exchanger tube ends extending through said partition into one of said housings for heat exchange contact with the cooling or heating gases, vapors, or condensed solids therein, said valves, ducts and blower means comprising a means for independently flowing said sublimate-laden vapors through said condensing-side for sublimate condensation and for flowing air or gas cooling or heating fluids through the air-side housing with controlled air or gas recirculation to provide selected temperature adjustment, with operation in either a cooling-condensing cycle or a heating-melting cycle and means for heating the air or gas flowing through said air-side housing when the exchanger is on the melting cycle, the said air-side flowing gas being hot enough to effect said melting, with said valve, duct and blower means controlling the flow to said housings to pass sublimate-laden gas to the condensing-side housing inlet of said system on the condensing mode and stopping flow thereof to the housing enlet of said system on the melting mode.

5. The apparatus as defined in Claim 4, wherein the heat-pipe tubes contain a wick structure to aid in the transport and distribution of the condensed working fluid within the tubes.

* * * * *

UNITED STATES PATENT AND TRADEMARK OFFICE
CERTIFICATE OF CORRECTION

PATENT NO. : 4,252,772

DATED : February 24, 1981

INVENTOR(S) : Peter F. Way

It is certified that error appears in the above—identified patent and that said Letters Patent is hereby corrected as shown below:

Column 1, line 35, "and" should read -- are --.

Column 1, line 67, "of" should read -- or --.

Column 5, line 66, after "similar" insert -- exchangers --.

Column 6, line 39, "opertion" should read -- operation --.

Column 7, line 65, after "by" insert -- a --.

Column 8, lines 18-24, these lines should be indented as the other parts of the claim.

Column 8, line 44, after "by" insert -- a --; same line 44, delete "or".

Column 10, line 5, "enlet" should read -- inlet --.

Signed and Sealed this

Fourth Day of August 1981

[SEAL]

Attest:

GERALD J. MOSSINGHOFF

Attesting Officer

Commissioner of Patents and Trademarks